United States Patent
Jiao et al.

(10) Patent No.: US 9,952,434 B2
(45) Date of Patent: Apr. 24, 2018

(54) DEVICE FOR ASSISTING VISUALLY IMPAIRED PATIENTS

(71) Applicants: Shuliang Jiao, Miami, FL (US); Rong Wen, Miami, FL (US)

(72) Inventors: Shuliang Jiao, Miami, FL (US); Rong Wen, Miami, FL (US)

(73) Assignee: The Florida International University Board of Trustees, Maimi, FL (US)

( * ) Notice: Subject to any disclaimer, the term of this patent is extended or adjusted under 35 U.S.C. 154(b) by 232 days.

(21) Appl. No.: 14/693,278

(22) Filed: Apr. 22, 2015

(65) Prior Publication Data
US 2016/0310325 A1    Oct. 27, 2016

(51) Int. Cl.
| | | |
|---|---|---|
| G02B 27/01 | (2006.01) | |
| G02B 27/00 | (2006.01) | |
| G02C 7/00 | (2006.01) | |
| H04N 5/225 | (2006.01) | |
| H04N 5/232 | (2006.01) | |
| A61F 2/14 | (2006.01) | |
| A61F 2/16 | (2006.01) | |

(52) U.S. Cl.
CPC .............. *G02B 27/017* (2013.01); *A61F 2/15* (2015.04); *G02B 27/0081* (2013.01); *G02C 7/00* (2013.01); *H04N 5/225* (2013.01); *H04N 5/23229* (2013.01); *A61F 2002/1696* (2015.04)

(58) Field of Classification Search
CPC .................................. G02B 27/01; A61F 9/08
See application file for complete search history.

(56) References Cited

U.S. PATENT DOCUMENTS

| | | | | |
|---|---|---|---|---|
| 5,728,156 | A * | 3/1998 | Gupta .................. | A61F 2/1648 351/159.17 |
| 9,028,067 | B1 * | 5/2015 | Fleischman ............ | A61B 3/113 351/209 |
| 2014/0210970 | A1 * | 7/2014 | Dalal ....................... | A61F 9/08 348/62 |
| 2015/0230979 | A1 * | 8/2015 | Serdarevic .............. | A61F 9/008 606/5 |
| 2015/0238362 | A1 * | 8/2015 | Chayet .................... | H04N 3/08 348/63 |
| 2016/0104453 | A1 * | 4/2016 | Borenstein ............... | G09G 5/02 348/62 |

\* cited by examiner

*Primary Examiner* — William C Vaughn, Jr.
*Assistant Examiner* — Jerry Jean Baptiste
(74) *Attorney, Agent, or Firm* — Saliwanchik, Lloyd & Eisenschenk

(57) ABSTRACT

The invention pertains to devices and methods that allow a subject having a diseased retina to see a more complete image of the subject's field-of-view. The invention provides a device comprising one or more windows comprising a plurality of optical components that redirect the light transmitting through the regions of the windows corresponding to the non-functional areas of the retina onto the functional areas of the retina in a manner such that the subject perceives a more complete field-of-view through the functional areas of the retina. The invention also provides a device comprising one or more cameras, a microprocessor, and one or more display screens, wherein the microprocessor comprises an algorithm programmed to remove portions of the image corresponding to non-functional areas of the subject's retina and compressing the portions so removed into the areas of the image corresponding to the functional areas of the subject's retina.

19 Claims, 5 Drawing Sheets

DEVICE FOR ASSISTING VISUALLY IMPAIRED PATIENTS

BACKGROUND OF INVENTION

Vision is based on photoreceptors sending electric impulses from defined regions of the retina to neuronal cells that pass through two lateral geniculate bodies and relay the impulses to defined regions in the primary visual cortex. Stereopsis is achieved by visual input from two eyes, which create slightly different images due to their differing viewing angles. In the absence of stereopsis, other cues to depth, including parallax, perspective, depth from movement, and occlusion, can be used to compensate and retain some depth perception.

The mechanisms employed by the brain to merge the images received from the two eyes are not fully understood. Convergence of the binocular input has been shown to occur beyond the geniculate bodies and to be a complex process that involves the primary visual cortex and other areas of the brain. Processes employed by the brain to deal with incongruent input from the two eyes are called adaptation processes. For example, studies in strabismus have shown that input from one eye that is weaker or out of register with input from the other eye, if not corrected early in infancy, can lead the brain to develop in a way that ignores the signal input from the weak or misdirected eye. Adaptation processes can be used therapeutically to "train" the eye to adjust to reorganized or distorted images.

Vision impairment is a major health concern with increasing numbers of aging and vision-impaired subjects. Age-related macular degeneration (AMD) and glaucoma are two eye diseases that cause visual disability and blindness. The macula comprises only four percent of the retinal area and contains the fovea, an area responsible for central, high resolution vision. AMD is the leading cause of visual disability and blindness in the population over 65 years of age in the United States and other Western countries. It affects 11% of the population of 65-74 year olds and 28% of the population over 74 years old.

AMD is generally divided into two forms, non-exudate, atrophic or dry AMD and neovasclar, exudate or wet AMD. Dry AMD, which constitutes more than 80% of all AMD cases, is characterized by drusen retinal pigment epithelium (RPE) atrophy, and cone photoreceptor degeneration. In geographic atrophy, the most severe form of dry AMD that accounts for >20% of blindness in North America, the central vision is severely affected but the peripheral vision in most subjects is relatively normal. No effective treatment is currently approved for dry AMD.

Glaucoma is a disease that causes a gradual degeneration of ganglion cell axons that make up the optic nerve and the retinal nerve fiber layer (RNFL). Vision loss usually begins in the retinal periphery and slowly progresses as the nerve cells die. According to National Eye Institute, among the U.S. population 40 years and older, there are 2.218 million open-angle glaucoma subjects (290,000 between the ages of 40 and 49). Owing to the rapid aging of the U.S. population, this number will increase to more than 3 million by 2020.

BRIEF SUMMARY

The subject invention provides devices and methods that allow a subject having a diseased retina to utilize functional areas of the retina to see a complete, or more complete, image of the field-of-view.

Certain embodiments of the invention provide a device comprising one or more windows comprising a plurality of optical components, wherein the optical components redirect the light transmitting through the regions of the windows corresponding to the non-functional areas of the retina onto the functional areas of the retina in a manner such that the subject perceives a more complete field-of-view through the functional areas of the retina. The optical components can be prisms, mirrors, and lenses. The device can comprise, for example, two windows and can be mountable onto the head of the subject.

Certain other embodiments of the invention provide a device comprising one or more cameras, a microprocessor, and one or more display screens and, optionally, a sensor to detect eye movement of the subject and accordingly adjust the field-of-view captured by the one or more cameras according to the subject's field-of-view. The microprocessor can comprise an algorithm programmed to transform the images received from the one or more cameras according to a map of the functional areas of the subject's retina, wherein the transformation comprises removing portions of the image corresponding to non-functional areas of the subject's retina and compressing the portions so removed into the areas of the image corresponding to the functional areas of the subject's retina.

BRIEF DESCRIPTION OF DRAWINGS

FIG. 5: An embodiment of the invention involving (1) changing the color, or contrast, or extracting the profile of the image as it would have been seen by the non-functional area of the retina; (2) overlapping the image as it would have been seen by the non-functional area of the retina with the image as it would have been seen by the functional area of the retina; and (3) projecting the overlapped images onto the functional area of the retina.

DETAILED DESCRIPTION OF THE INVENTION

Figure 1:
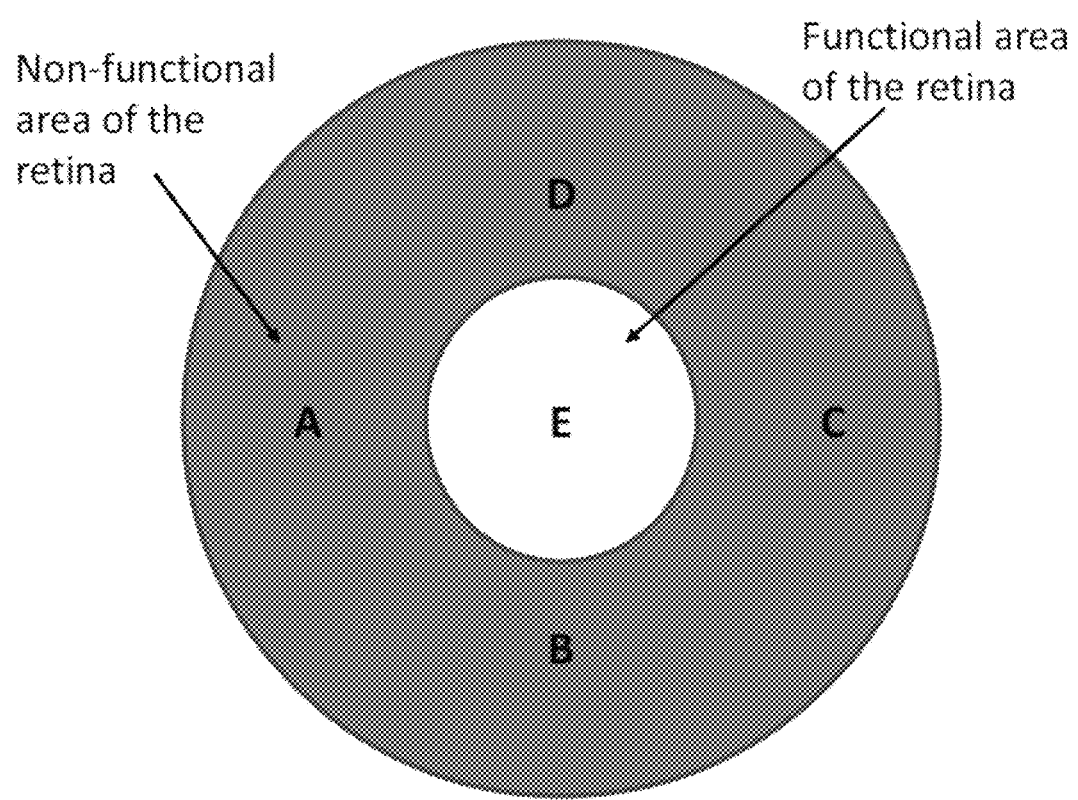
FIG. 1. Schematic representation of the retina having a functional area and a non-functional area.
Figure 2:
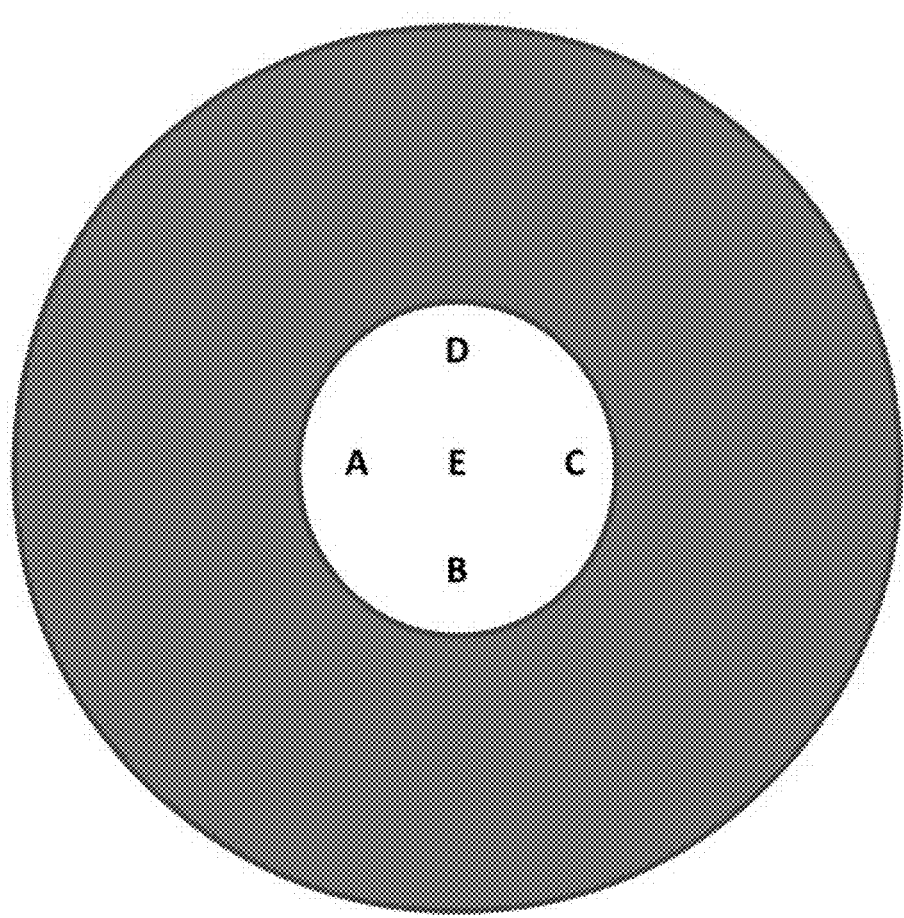
FIG. 2: An embodiment of the invention demonstrating shrinking the image and projecting the shrunk image on to the functional area of the retina.
Figure 3:
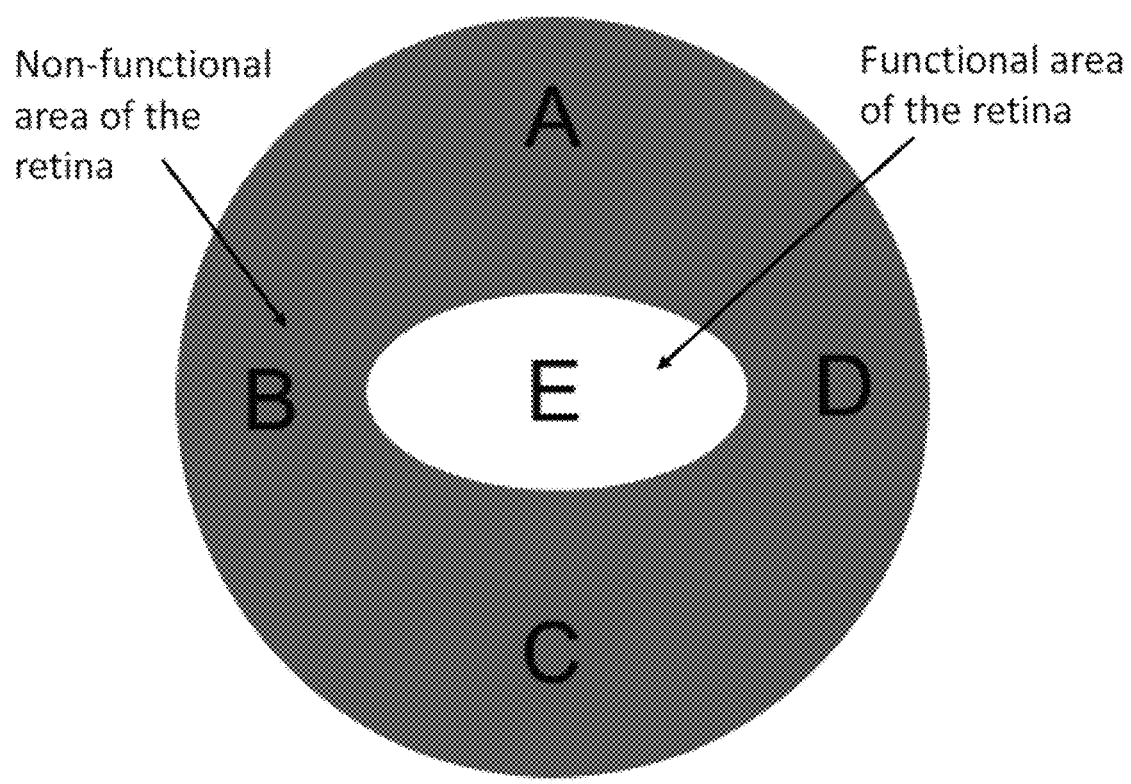
FIG. 3. Schematic representation of the retina in which the non-functional area is irregular or non-circular.
Figure 4:
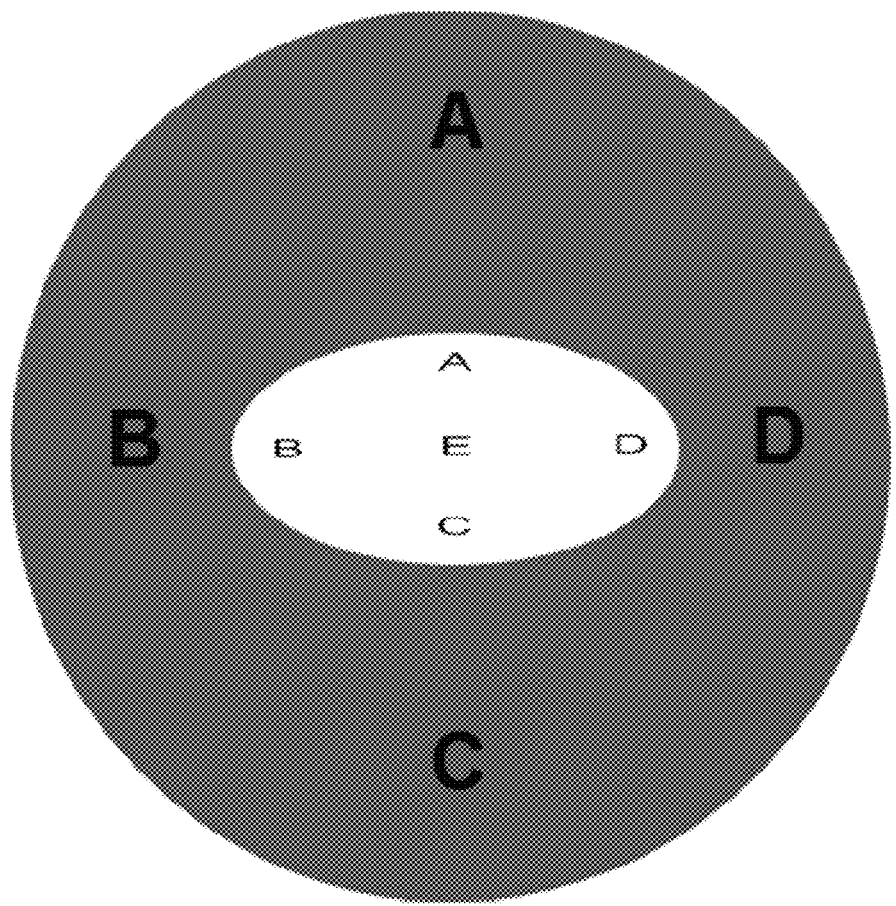
FIG. 4. An embodiment of the invention demonstrating modifying the image and projecting the modified image on the functional area of the retina.

In one embodiment the invention provides a device, for example, a non-invasive device, that facilitates a subject with impaired vision, for example, impaired central or impaired peripheral vision, to see better. In a preferred embodiment, the device of the invention obtains one or more images from the field-of-view of the subject, manipulates the image(s) and projects the manipulated image(s) onto the functional area(s) of the subject's retina while avoiding image projection onto the non-functional areas of the subject's retina.

Central vision impairment is commonly caused by age-related macular degeneration (AMD); whereas, peripheral vision impairment is often caused by glaucoma. In one embodiment, the device of the invention manipulates the image of the field-of-view of a subject and projects the manipulated image onto the functional area(s) of a subject's retina, for example, the peripheral retina in an AMD subject and central retina in a glaucoma subject, to facilitate the subject seeing a more complete image of the field-of-view.

The devices of the invention can be used in a subject, for example, a human or a non-human animal. Non-limiting examples of non-human animals include dogs, cats, horses, cattle, pigs, non-human primates, etc.

In one embodiment of the invention, the subject has undergone tests to determine the distribution of regions containing functional photoreceptors in the subject's retina(s). Non-limiting examples of such tests include fundus diagnostic and multifocal electroretinogram (ERG). Additional methods of determining functional and non-functional areas in a subject's retina are well known to a person of ordinary skill in the art and such embodiments are within the purview of the subject invention.

Depending on the subject's condition or disease, functional areas may be localized either in the central area of the retina including the macula (e.g., in a subject suffering from glaucoma), or in peripheral areas of the retina (e.g., in subjects suffering from AMD).

One embodiment of the invention provides a device that allows a subject having a diseased retina to utilize functional areas of the retina to see a more complete image of the field-of-view. The device comprises one or more windows comprising a plurality of optical components, wherein the optical components distribute the light transmitting through the regions of the windows corresponding to the non-functional areas of the retina onto the functional areas of the retina in a manner such that the subject perceives a more complete field-of-view through the functional areas of the retina. The optical components can be prisms, mirrors, and/or lenses. In one embodiment, the device comprises two windows—one window corresponding to each eye of the subject.

For the purposes of this invention, the term "corresponding to the non-functional areas of the retina" refers to the portions of the field-of-view or the portions of the image of the field-of-view which would have been seen by the non-functional areas of the retina if the non-functional areas were functional. Similarly, for the purposes of this invention, the term "corresponding to the functional areas of the retina" refers to the portions of the field-of-view or the portions of the image of the field-of-view which is seen by the functional areas of the retina.

In a further embodiment, the device is mountable onto the head of the subject. In certain embodiments, the device comprises windows that are mounted in a frame having side arms adapted to run alongside the subject's head. The device may be configured to be similar to, for example, goggles or eye-glasses.

One embodiment of the invention provides eye-wear comprising optical components, e.g., prisms, semi-transparent mirrors and lenses. The optical components, are arranged in a manner that the light coming from the field-of-view of a subject and transmitting through the eye-wear is projected onto defined areas based on the functional regions in the retina of the subject. For example, the optical components can be arranged in a manner that redirects the light from the region corresponding to non-functional area of the subject's retina onto the functional area of the subject's retina so that the image of the subject's entire field-of-view is produced on the functional area of the subject's retina.

In one embodiment, the optical components are arranged in a manner that redirects the light corresponding to the central portion of the subject's retina onto the peripheral portion of the subject's retina. Accordingly, the subject having non-functional central retina can perceive a more complete field-of-view through the functional peripheral portion of the retina.

In another embodiment, the optical components are arranged in a manner that redirects the light corresponding to the peripheral portion of the subject's retina onto the central portion of the subject's retina. Accordingly, the subject having non-functional peripheral retina area(s) can perceive a more complete field-of-view through the functional central portion of the retina.

As noted above, functional regions in the retina of a subject can be predetermined, based on, for example, multifocal ERG examination. Therefore, the optical components of the eye-wear can be arranged in a manner customized to a subject depending on functional and non-functional areas in the subject's retina.

A further embodiment of the invention provides a device comprising one or more cameras, a microprocessor, and one or more display screens. In one embodiment, the device comprises two video cameras (one for each eye), two display screens (one for each eye), and a microprocessor. In one embodiment, the device further comprises a sensor to detect eye movement of the subject and accordingly adjust the field-of-view captured by the one or more cameras. For example, the sensor can measure the point of gaze and adjust the direction of the video cameras to match the subject's field-of-view.

In certain embodiments, the images obtained by each video camera are transmitted to a microprocessor, where the microprocessor transforms the images according to an algorithm. In one embodiment the microprocessor is integral to the device. In a further embodiment, the microprocessor is mountable onto the head of the subject along with the rest of the components of the device. In certain embodiments, the microprocessor is separate from the rest of the components of the device and communicates with the device through a wireless connection or a physical connection.

A map of the functional areas in the retina of a subject such as, for example, a multifocal ERG-generated map, is input into the algorithm and the algorithm is programmed to transform, the images obtained from the camera to align the images with the functional areas of the retina of the subject.

For the purposes of this invention, the terms "transform" or "manipulate" an image or synonyms thereof indicate that the algorithm removes the portions of the image corresponding to non-functional areas of the subject's retina and directs that information into the areas of the image corresponding to the functional areas of the subject's retina.

In one embodiment, the subject's retina is not functional in the central portion and the algorithm removes the central portion of the image and redirects the portion so removed into the peripheral portion of the image. Accordingly, the processed image appears distorted to a normal eye having no visual information in the central portion and having redirected visual information in the peripheral portion.

In another embodiment, the subject's retina is not functional in the peripheral portion and the algorithm removes the peripheral portion of the image and redirects the portion so removed into the central portion of the image. As such, the processed image would appear distorted to a normal eye having no visual information in the peripheral portion and having redirected visual information in the central portion.

In a further embodiment, the subject's retina has intermittent functional and non-functional areas, for example, spots or islands of non-functional areas, and the algorithm removes the portions of the image corresponding to non-functional areas of the retina and redirects those images into the portions of the image corresponding to the functional areas of the retina. Accordingly, the processed image would appear distorted to a normal eye having no visual information in the certain portions, which appear as holes in the processed image, and having re-directed visual information in certain other portions of the processed image, which appear as contours of re-directed visual information.

In one embodiment, the algorithm is programmed to transform the image in a horizontal and/or vertical direction. In another embodiment, the algorithm is programmed to transform the image in one direction first and then further transform the image in another direction. For example, the algorithm can be programmed to transform the image in the horizontal direction and then further transform the image in the vertical direction.

In further embodiments of the invention, depth perception is created using separate images from each eye. Separate images can be created using dual video inputs, thereby providing a completely separate video signal for each eye.

In certain other embodiments, two separate video signals are combined into one signal by alternating left and right images in successive frames. In yet other embodiments, two separate video signals are combined into one signal by using half of each image from one camera, for example, the left-eye camera, and the other half of the image from the other camera, for example, the right-eye camera. In further embodiments, the halves of the images can be allocated side-by-side or top-to-bottom.

In preferred embodiments of the subject invention, the microprocessor transforms the images received from the video cameras aligned with both eyes and transmits contours of the images to the display screens for each eye. In some embodiments, the contours originate from central parts of the image. In other embodiments, the contours originate from peripheral parts of the image.

In a further embodiment, the microprocessor transmits the images transformed by the algorithm to one or more display screens. In one embodiment, the device has two screens (one for each eye).

In one embodiment, the display screens are semi-transparent. Semi-transparent screens permit the subject to merge the images projected onto the screen with the images perceived by the subject naturally, i.e., without processing by the device.

In other embodiments, the display screens are non-transparent. Therefore, the image displayed consists exclusively of the transformed image generated by the microprocessor.

In one embodiment, the device has two screens, one of which is semi-transparent and the other one is not transparent depending on the degree of vision in the corresponding eyes of the subject. Therefore, the image perceived by the subject is a mixed image originating in part from the real world image perceived by the subject naturally through the semi-transparent screen, i.e., without processing by the device, and in part from the transformed image generated by the microprocessor.

In some embodiments, the display screens are selected from Digital Micromirror Devices (DMDs), liquid crystal displays (LCDs), light emitting diode (LED) display or analog displays, which project the images onto the retinas. Functioning and design of a DMD, LCD, LED, and analog displays that can be utilized in the devices of the current invention are well known to a person of ordinary skill in the art.

The invention can be used in subjects suffering from glaucoma or AMD as well as subjects suffering from other eye diseases affecting retinal function, for example, subjects exhibiting retinal degeneration with residual areas of functional photoreceptors. Since the microprocessor algorithm can be programmed individually for each subject, retinal maps with discrete areas of degeneration can be used to instruct the microprocessor algorithm on image transformation to allow a subject to view a complete field-of-view.

A person of ordinary skill in the art can further appreciate that adaptation processes in the brain can enable a subject to "train" to recognize the contours originating from parts of the image, which parts the subject is unable to see due to retinal degeneration, and create a full point of view image.

It should be understood that the embodiments described herein are for illustrative purposes only and that various modifications or changes in light thereof will be suggested to the skilled artisan and are to be included within the spirit and purview of this application.

EXAMPLES

Following are examples that illustrate embodiments and procedures for practicing the invention. These examples should not be construed as limiting.

Example 1

A multifocal ERG-generated map of a subject's retinal areas with functional photoreceptors and retinal areas with degenerated photoreceptors is generated during a fundus examination. A subject is fitted with head-mounted goggles equipped with prisms, mirrors and lenses to capture the light transmitted through the goggles and to project the transmitted light to functional areas of the subject's retinas and avoid non-functional areas of the subject's retinas.

Example 2

A multifocal ERG-generated map of a subject's retinal areas with functional photoreceptors and retinal areas with degenerated photoreceptors is generated during a fundus examination. A programmable microprocessor is instructed according to the ERG-generated retinal map of the subject as to the distribution of functional photoreceptors in the subject's retinas.

The subject is fitted with a device comprising two video cameras and two display screens aligned with each eye and a movement detection sensor mounted on a goggle like frame. The movement detection sensor instructs the video cameras to point in the direction of the gaze of the subject. Each video camera captures the image looked at by the respective eye and sends the image to the programmable microprocessor.

The programmable microprocessor receiving images from both eyes and containing information about the retinal maps of both eyes, applies the programmed algorithm to transform the images according to the distribution of the subject's functional photoreceptors, aligns the images for stereopsis, and transmits the final images to the semi-transparent display screens in front of each eye. The transformed images displayed by the semi-transparent display screens are projected onto functional areas of the subject's retinas. The subject is trained to recognize the transformed image as a complete image of the field-of-view.

In a subject suffering from AMD, the microprocessor algorithm is programmed to specifically capture the portions of the image that would be perceived by the macular area of a normal retina and project the transformed image onto peripheral areas of the AMD affected retina, which peripheral areas contain functional photoreceptors.

In a subject suffering from glaucoma, the microprocessor algorithm is programmed to specifically capture the portions of the image that would be perceived by the peripheral areas of a normal retina and project the transformed image onto the central areas, including the macula, which contain functional photoreceptors.

Example 3

A subject is fitted with a head-mounted device comprising two video cameras, a movement sensor, a microprocessor and two semi-transparent display screens. Each video camera captures the image looked at by the respective eye and sends the image to the programmable microprocessor.

The programmable microprocessor receiving images from both cameras and based on the ERG-generated retinal map of the subject's retina, applies the algorithm to generate contours of the portions of the image that would project on functional areas of the retina. The contours of the image are aligned for stereopsis and transmitted to the semi-transparent display screens in front of each eye. The contour images are superimposed onto the functional areas of the subject's retinas, which functional areas also receive real world images through the semi-transparent goggles.

The subject being trained on discerning the contours and real world views and thus being able to allocate the contours to the areas of the image that are missing in the real world views due to the subject's retinal degeneration, perceives a more complete image of the field-of-view.

In accordance with disease progression, the microprocessor is periodically adjusted to account for changes in the distribution of functional photoreceptors in the subject's retinas.

All patent applications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to subjects skilled in the art and are to be included within the spirit and purview of this application.

We claim:

1. A device that allows a subject having diseased retina to utilize a functional area of the retina to see a more complete image of the subject's field-of-view, the device comprising: one or more cameras, a microprocessor, and one or more display screens,
    wherein the microprocessor comprises an algorithm programmed to transform the images received from the one or more cameras according to a map of the functional area of the subject's retina, wherein the transformation of the images comprises:
    a) removing portions of the images corresponding to a non-functional area of the subject's retina;
    b) modifying a color and/or contrast of the portions of the images corresponding to the non-functional area of the subject's retina;
    c) generating contours of the portions of the images corresponding to the non-functional area of the subject's retina; and
    d) overlapping the modified portions of the images from step b) and the contours from step e) with portions of the images corresponding to the functional area of the subject's retina to produce transformed images; and
    wherein the device projects the transformed images onto the functional area of the subject's retina.

2. The device of claim 1, further comprising a sensor to detect eye movement of the subject and accordingly adjust the field-of-view captured by the one or more cameras according to the subject's field-of-view.

3. The device of claim 1, wherein the algorithm is programmed to invert the image before transformation.

4. The device of claim 1, wherein the subject's retina is not functional in the central portion and the algorithm removes the central portions of the images and modifies and overlaps the portions so removed into the peripheral portions of the images.

5. The device of claim 1, wherein the subject's retina is not functional in the peripheral portion and the algorithm removes the peripheral portions of the images and modifies and overlaps the portions so removed into the central portions of the images.

6. The device of claim 1, wherein the subject's retina has intermittent functional and non-functional areas and the algorithm removes the portions of the image corresponding to non-functional areas of the retina and modifies and overlaps the portions so removed into the portions of the image corresponding to the functional area of the retina.

7. The device of claim 1, wherein the device produces separate images for each eye of the subject, and wherein the separate images are obtained from each of the two cameras.

8. The device of claim 1, wherein the two images from each of the two cameras are combined into one image by alternating left and right images in successive frames.

9. The device of claim 1, wherein the two images obtained from each of the two cameras are combined into one image by using half of the image from one camera and the other half of the image from the other camera.

10. The device of claim 1, wherein the one or more display screens are selected from Digital Micromirror Device (DMD), liquid crystal display (LCD), light emitting diode (LED) display, and analog display.

11. The device of claim 1, wherein the device is mountable onto the head of the subject.

12. The device of claim 1, wherein the microprocessor communicates with the rest of the components through a wireless connection or a physical connection.

13. A method for improving vision of a subject having a diseased retina having a functional area and a non-functional area, the method comprising providing to the subject a device that allows the subject to utilize the functional area of the retina to see a more complete image of the subject's field-of-view, the device comprising: one or more cameras, a microprocessor, and one or more display screens,
    wherein the microprocessor comprises an algorithm programmed to transform the images received from the one or more cameras according to a map of the functional areas-area of the subject's retina, wherein the transformation of the images comprises:
    a) removing portions of the images corresponding to the non-functional area of the subject's retina;
    b) modifying a color and/or contrast of the portions of the images corresponding to the non-functional area of the subject's retina;
    c) generating contours of the portions of the images corresponding to the non-functional area of the subject's retina; and d) overlapping the modified portions of the images from step b) and the contours from step c) with the portions of the images corresponding to the functional area of the subject's retina to produce transformed images; and wherein the device projects the transformed images onto the functional area of the subject's retina.

14. The method of claim 13, wherein the algorithm is programmed to invert the image before transformation.

15. The method of claim 13, wherein the subject's retina has intermittent functional and non-functional areas and the algorithm removes the portions of the images corresponding to non-functional areas of the retina and modifies and overlaps the portions so removed into the portions of the images corresponding to the functional areas of the retina.

16. The method of claim 13, wherein the device produces separate images for each eye of the subject, wherein the separate images are obtained from each of the two cameras.

17. The method of claim 13, wherein the two images from each of the two cameras are combined into one image by alternating left and right images in successive frames.

18. The method of claim 13, wherein the two images obtained from each of the two cameras are combined into one image by using half of the image from one camera and the other half of the image from the other camera.

19. A device that allows a subject having a diseased retina comprising a functional central area and a non-functional peripheral area, wherein the device allows the subject to see a more complete image of the subject's field-of-view, the device comprising: one or more cameras, a microprocessor, and one or more display screens, wherein the microprocessor comprises an algorithm programmed to transform the images received from the one or more cameras according to a map of the functional areas-central area of the subject's retina, wherein the transformation of the images comprises:

a) removing portions of the images corresponding to the non-functional peripheral area of the subject's retina;

b) modifying a color and/or contrast of the portions of the images corresponding to the non-functional peripheral area of the subject's retina;

c) generating contours of the portions of the images corresponding to the non-functional peripheral area of the subject's retina; and d) overlapping the modified portions of the images from step b) and the contours from step c) with the portions of the images corresponding to the functional central area of the subject's retina to produce transformed images; and wherein the device projects the transformed images onto the functional central area of the subject's retina.

* * * * *